(12) United States Patent
Takahashi et al.

(10) Patent No.: US 7,973,280 B2
(45) Date of Patent: Jul. 5, 2011

(54) COMPOSITE CHARGED PARTICLE BEAM APPARATUS, METHOD OF PROCESSING A SAMPLE AND METHOD OF PREPARING A SAMPLE FOR A TRANSMISSION ELECTRON MICROSCOPE USING THE SAME

(75) Inventors: Haruo Takahashi, Chiba (JP); Yutaka Ikku, Chiba (JP); Yo Yamamoto, Chiba (JP); Kouji Iwasaki, Chiba (JP)

(73) Assignee: SII Nanotechnology Inc. (JP)

( * ) Notice: Subject to any disclaimer, the term of this patent is extended or adjusted under 35 U.S.C. 154(b) by 316 days.

(21) Appl. No.: 12/378,138

(22) Filed: Feb. 11, 2009

(65) Prior Publication Data

US 2009/0206254 A1 Aug. 20, 2009

(30) Foreign Application Priority Data

Feb. 15, 2008 (JP) .................................. 2008-035048

(51) Int. Cl.
*G01N 23/00* (2006.01)
*H01J 27/00* (2006.01)

(52) U.S. Cl. ..................... 250/307; 250/492.21; 250/311

(58) Field of Classification Search .......... 250/306–311, 250/492.21
See application file for complete search history.

(56) References Cited

U.S. PATENT DOCUMENTS

| | | | |
|---|---|---|---|
| 5,656,811 A * | 8/1997 | Itoh et al. | 850/43 |
| 2003/0089852 A1 * | 5/2003 | Ochiai et al. | 250/310 |
| 2004/0108458 A1 * | 6/2004 | Gerlach et al. | 250/311 |
| 2008/0061233 A1 * | 3/2008 | Ogawa | 250/307 |

* cited by examiner

*Primary Examiner* — Jack I Berman
*Assistant Examiner* — David Smith
(74) *Attorney, Agent, or Firm* — Adams & Wilks (57) ABSTRACT

An apparatus is provided that precisely conduct ion beam etching to a sample having the properties of which easily change by electron beam irradiation with no loss of ease of operation and throughput. An apparatus includes an ion beam lens barrel and an electron beam lens barrel, which can observe or measure the conditions of a sample with an electron beam in the process of etching with an ion beam, wherein first, an observation image is obtained that includes the entire process area formed by secondary signals generated by an electron beam, secondly, an irradiation permit area and an irradiation inhibit area are defined in the observation image, and thirdly, electron beam irradiation is restricted only to the irradiation permit area.

9 Claims, 5 Drawing Sheets

COMPOSITE CHARGED PARTICLE BEAM APPARATUS, METHOD OF PROCESSING A SAMPLE AND METHOD OF PREPARING A SAMPLE FOR A TRANSMISSION ELECTRON MICROSCOPE USING THE SAME

BACKGROUND OF THE INVENTION

The present invention relates to a composite charged particle beam apparatus that observes the cross section of a sample or prepares a thin piece sample for a transmission electron microscope (TEM), and a method of processing a sample and a method of preparing a sample for a transmission electron microscope using the same.

Because a focused ion beam apparatus can conduct highly precise micromachining, the apparatus is variously applied to micromachining including TEM sample preparation for a thin piece. In conducting such micromachining, as disclosed in Patent Reference 1, such a method is proposed that an apparatus having a scanning electron microscope and a focused ion beam apparatus combined is used for micromachining while a sample is observed (see Japanese Patent No. 2811073). Because this method is characterized in that highly precise processing can be reliably conducted while the conditions of a sample are kept track of, this method is widely conducted.

However, there are samples having the properties of which easily change because of electron beam irradiation for contraction including low dielectric constant materials for use in semiconductors having, for example. To these samples, it is difficult to apply the method that conducts focused ion beam processing while the sample is observed through a scanning electron microscope. There are many demands for highly precise micromachining even to materials having the properties of which easily change because of electron beam irradiation, and it is desired to implement highly precise micromachining to these materials. For one solution, as described in Non-Patent Reference 1, such a method is also proposed that processing is conducted while a sample is cooled (see Suzuki, "Application of Preparing TEM samples by Dual Beam FIB", 21st Analytical Electron Microscope Symposium Abstract, pp. 69-72, 2005). However, this method has a problem that processing takes time because the operation of a sample stage has limitations and the method includes the process steps of cooling a sample and returning the temperature of the sample to a room temperature.

SUMMARY OF THE INVENTION

In consideration of the problems of the techniques before, an object of the invention is to provide means for precisely conducting ion beam etching to a sample having the properties of which easily change because of electron beam irradiation with no loss of ease of operation and throughput.

In order to solve the problems, a first aspect of the invention is a composite charged particle beam apparatus including: an ion beam lens barrel configured to etch a sample with an ion beam; an electron beam lens barrel configured to irradiate an electron beam onto a given area on the sample; a secondary signal detector configured to detect a secondary signal generated by electron beam irradiation; a data processing unit configured to associate a position to irradiate an electron beam with an amount of secondary signals for imaging; an image display unit configured to display thereon an image of a given area on the sample based on an image signal from the data processing unit; an irradiation position setting means for defining an irradiation permit area or an irradiation inhibit area specified by an input device as electron beam irradiation position data; and an irradiation position control unit configured to control a position to irradiate an electron beam based on electron beam irradiation position data from the irradiation position setting means, wherein the irradiation position setting means updates electron beam irradiation position data depending on whether the specified area is an irradiation permit area or an irradiation inhibit area, whereby the irradiation position control unit restricts electron beam irradiation only to the irradiation permit area.

In order to solve the problems, a second aspect of the invention is the composite charged particle beam apparatus according to the first aspect, wherein the irradiation position setting means updates electron beam irradiation position data from the irradiation permit area and the irradiation inhibit area, both areas specified by the input device, in an image including an entire etching process area obtained by ion beam scanning in advance.

In order to solve the problems, a third aspect of the invention is the composite charged particle beam apparatus according to the first aspect, wherein during processing with an ion beam, the irradiation position setting means estimates an electron beam irradiation permit area from an image at a position apart from a process target area and information already known about a sample process target portion.

In order to solve the problems, a fourth aspect of the invention is the composite charged particle beam apparatus according to the first aspect, wherein the secondary signal detector is capable of detecting a secondary signal generated by ion beam irradiation, the data processing unit associates an ion beam irradiation position with an amount of secondary signals for imaging, and the irradiation position setting means defines an electron beam irradiation permit area and an electron beam irradiation inhibit area based on a relationship between relative positions of an ion beam and an electron beam from an observation image with an ion beam.

In order to solve the problems, a fifth aspect of the invention is a method of processing a sample using the composite charged particle beam apparatus according to any one of the aspects, the method including the steps of: setting a position recognition target in an observation image of an irradiation permit area; detecting a relative position shift between a position of a sample and a position to irradiate an electron beam based on a movement of the target; and correcting a position of the irradiation permit area.

In order to solve the problems, a sixth aspect of the invention is a method of processing a sample using the composite charged particle beam apparatus according to any one of the aspects, the method including the steps of: detecting an amount of secondary signals from an irradiation permit area; and terminating ion beam etching when an amount of secondary signals reaches a predetermined amount.

In order to solve the problems, a seventh aspect of the invention is the method of processing a sample using the composite charged particle beam apparatus according to the sixth aspect, the method including the steps of: obtaining an observation image formed by secondary signals generated by an electron beam, the image including an entire process area; defining a thickness monitoring area and a reference area as an irradiation permit area in the observation image; irradiating an electron beam only onto the irradiation permit area; and detecting a secondary charged particle generated in the thickness monitoring area and the reference area, calculating thickness information about the thickness monitoring area from amounts of the detected secondary charged particles, and terminating ion beam etching when the calculated thickness reaches a consumed thickness.

In order to solve the problems, an eighth aspect of the invention is a method of preparing a sample for a transmission electron microscope using a composite charged particle beam apparatus, the apparatus including: an ion beam lens barrel configured to etch a sample with an ion beam; an electron beam lens barrel configured to irradiate an electron beam onto a given area on the sample; a secondary signal detector configured to detect a secondary signal generated by electron beam irradiation; a data processing unit configured to associate a position to irradiate an electron beam with an amount of secondary signals for imaging; and an image display unit configured to display thereon an image of a given area on the sample based on an image signal from the data processing unit, wherein a condition of a sample in the process of etching with an ion beam is observed, the method including: after conducting etching with an ion beam to prepare a sample with a thin piece portion having a predetermined thickness thicker than a finishing thickness; a first step of obtaining an electron beam observation image of an entire cross section of the thin piece portion; a second step of defining an irradiation area and an irradiation inhibit area in the observation image; and a third step of cutting a thin piece in the finishing thickness while the thickness is monitored as irradiation of the electron beam is restricted only to the irradiation permit area.

In order to solve the problems, a ninth aspect of the invention is a method of preparing a sample for a transmission electron microscope using a composite charged particle beam apparatus, the apparatus including: an ion beam lens barrel configured to etch a sample with an ion beam; an electron beam lens barrel configured to irradiate an electron beam onto a given area on a sample; a secondary signal detector configured to detect a secondary signal generated by electron beam irradiation; a data processing unit configured to associate a position to irradiate an electron beam with an amount of secondary signals for imaging; and an image display unit configured to display thereon an image of a given area on the sample based on an image signal from the data processing unit, wherein a condition of a sample in the process of etching with an ion beam is observed, the method including the steps of: forming a hole on both sides of a thin piece portion in a trapezoidal shape in which the thin piece portion is an upper base of the trapezoidal shape of the hole seen from the top side of a sample when the thin piece portion is prepared with an ion beam in a predetermined thickness thicker than a finishing thickness; obtaining an observation image that is a part of a shape having a side connecting to a bottom base of the trapezoidal shape with respect to the hole on both sides while a rectangular electron beam scan area is brought close to a hole process portion on both sides from outside the hole process portion on both sides in parallel to the thin piece portion; determining an electron beam irradiation inhibit area and an electron beam irradiation permit area in a thin piece portion cross section from the observation image and a length of the thin piece portion; and irradiating an electron beam onto the electron beam irradiation permit area to cut the thin piece portion in a finishing thickness with an ion beam while the thickness is monitored.

According to the invention, to a sample including a material which may not be suited to electron beam irradiation, such as materials having the properties of which easily change because of electron beam irradiation and materials in which charge-up tends to occur, electron beam irradiation to a specific portion can be reduced significantly. Therefore, the invention can provide means for precisely conducting ion beam etching to a sample including materials having the properties of which easily change and materials which may not be suited to electron beam irradiation with no loss of ease of operation and throughput.

DESCRIPTION OF THE PREFERRED EMBODIMENTS

Hereinafter, preferred embodiments for implementing the invention will be described with reference to the drawings.

In addition, the descriptions of the embodiments are only examples, and the configuration of the invention will not be limited to the descriptions below.

Embodiment 1

Figure 1:
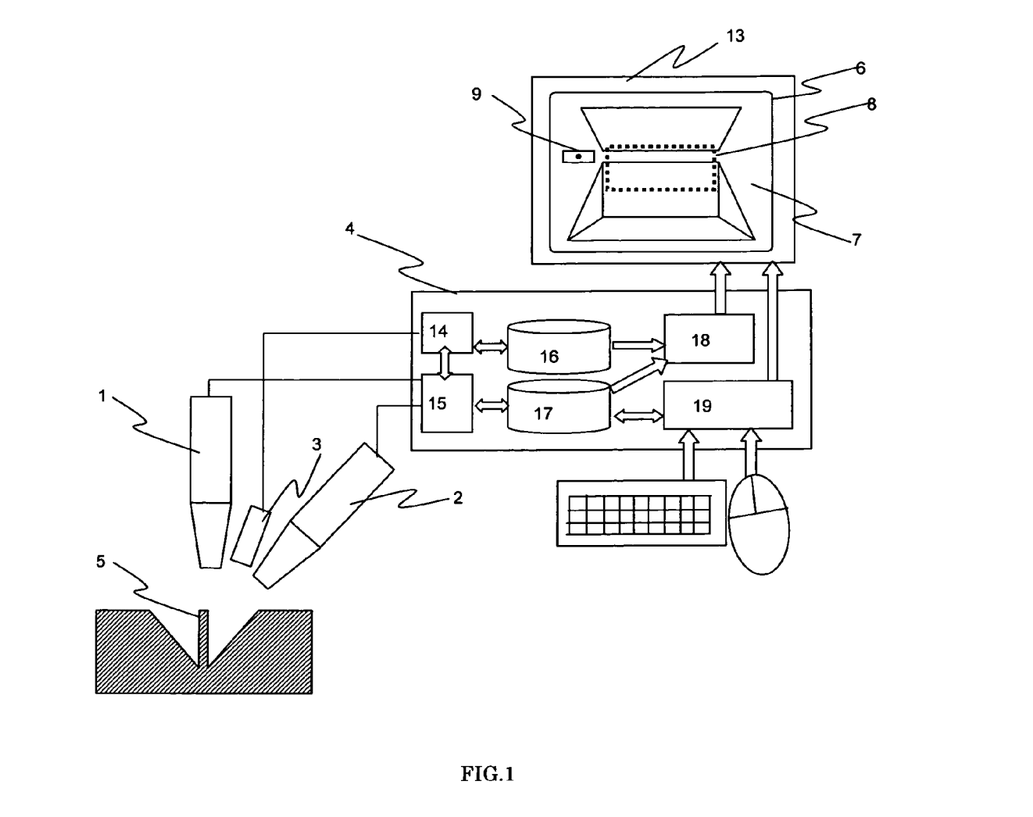
FIG. 1 shows a diagram illustrative of the configuration of a composite charged particle beam apparatus according to the invention.

FIG. 1 shows a composite charged particle beam apparatus according to the invention.

As shown in FIG. 1, the composite charged particle beam apparatus according to the invention is configured of an ion beam lens barrel 1, an electron beam lens barrel 2, a secondary signal detector 3, and a data processing unit 4. The data processing unit 4 includes irradiation position data 17 that defines positions to be scanned by an electron beam, an irradiation position control unit 15 that controls the ion beam lens barrel 1 or the electron beam lens barrel 2 to irradiate an ion beam or an electron beam onto a desired location based on the irradiation position data 17, a signal intensity acquiring unit 14 that associates the signal intensity from the secondary signal detector 3 with the beam irradiation position and stores them as signal intensity data 16, an image display means 18 for displaying the signal intensity data 16 as an image, an image display device 13 that displays an image thereon based on signals from the image display means 18, and an irradiation position setting means 19 for specifying an irradiation permit area and an irradiation inhibit area on the image on the image display device 13 to change the corresponding irradiation position data 17.

In this embodiment, for the ion beam lens barrel 1, a focused ion beam lens barrel is used which uses liquid metal gallium as an ion source, and for the electron beam lens barrel 2, the lens barrel of a scanning electron microscope is used.

The irradiation position data 17 is defined as a combination of numeric value data that generates reference voltage to control the deflector of the ion beam lens barrel 1 or the electron beam lens barrel 2 by a digital-to-analog converter (DAC) with data that indicates the residence time of the beam and the timing of switching ON/OFF of the beam. The irradiation position control unit 15 is mounted as an electronic circuit that sequentially reads irradiation position data and controls output to the deflector and the control signals of turning ON/OFF the beam onto the irradiation position at the timing based on read data. The signal intensity acquiring unit 14 is mounted as an electronic circuit that receives data of the current irradiation position from the irradiation position control unit 15 and writes data of output voltage after AD conversion from the secondary signal detector 3 to the memory address corresponding to the irradiation position. The image display means 18 is mounted as image display software that converts signal intensity data into image information processable by a multipurpose computer and then an image is displayed. The irradiation position setting means 19 is mounted as software that uses an input device such as a keyboard and a mouse to interactively specify areas on the displayed image and software that updates the irradiation position data depending on whether the specified area is an irradiation permit area or an irradiation inhibit area.

The ion beam lens barrel 1 and the electron beam lens barrel 2 are arranged with respect to a thin piece sample 5 of a process target in such a way that beams cross each other at the position of the sample so that the conditions of the sample can be checked while the sample is being cut into a thin piece. Generally, the cross section produced by FIB is prepared in the orientation in which the cross section is the front facing to SEM. For the secondary signal detector 3, a secondary electron detector is used that is capable of detecting secondary electrons emitted from the sample.

As shown in FIG. 1, cutting a thin piece is conducted in such a way that both sides of the thin piece sample 5 is cut by ion beam etching to leave the thin piece sample 5. Although there are various thicknesses of the thin piece, in the case of the sample for use in transmission electron microscopic observation of typical semiconductor devices, the thickness is 100 nm or thinner in most cases.

Figure 2:
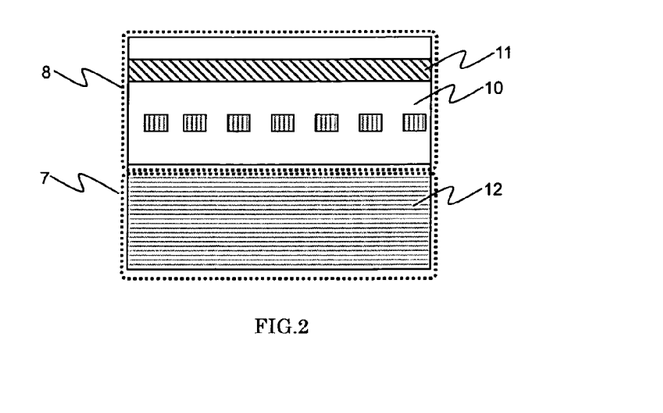
FIG. 2 shows a structural diagram depicting the section of a thin piece sample.

FIG. 2 shows a schematic diagram depicting the cross section of a typical semiconductor device. As shown in the drawing here, the upper part is an interconnect layer including a low dielectric constant interlayer insulating film 10 and a wiring 11, and a lower part is a substrate 12 including a diffusion layer. In this device, it is known that an electron beam is applied onto the interconnect layer including the low dielectric constant interlayer insulating film, and then changes such as contraction occur in the properties of the interlayer insulating film. On this account, it is desired not to irradiate the electron beam onto the interconnect layer as much as possible.

In this embodiment, first, at the point in time at which the remaining thickness of the thin piece sample 5 is a few hundreds nm or above, the electron beam lens barrel 2 scans the area including the thin piece sample 5 with the electron beam only one time to obtain an observation image 6 on the image display device 13. Referring to FIG. 1, irradiation position data 17 indicating the rectangular area including the entire process area is prepared, the irradiation position control unit 15 is used to irradiate the beam onto the rectangular area, the signal intensity acquiring unit 14 acquires the secondary signal intensity at each irradiation point, and the image display means 18 is used to display the observation image of the entire process area on the image display device 13. Observation is conducted while the thickness of the thin piece sample 5 is still thick. This is because it can be considered that even though the surface of the sample is adversely affected more or less, the adversely affected portion is cut in the process of cutting a thin piece in the subsequent steps, and because cutting can be controlled sufficiently on the observation image through the ion beam lens barrel 1 while the thickness of the thin piece sample 5 is still thick.

Secondly, in the observation image 6, the area including the area in which the cross section of the interconnect layer is exposed is defined as an electron beam irradiation inhibit area 8, and the other area is defined as an electron beam irradiation permit area 7. More specifically, an area is defined on an image, and the irradiation position setting means 19 updates the irradiation position data 17 corresponding to the defined area.

Thirdly, a thin piece is being cut by the ion beam lens barrel 1 while observation is conducted sequentially through the electron beam lens barrel 2. Because the irradiation position data 17 is updated to such data that the beam is applied only onto the irradiation permit area whereas the beam is not applied onto the irradiation inhibit area, in observation at this time, the electron beam is not applied onto the electron beam irradiation inhibit area 8. By this observation, phenomena such as the curve of the sample, holes in the sample caused by excessive ion beam etching, and a beam position shift, or signs of these phenomena can be detected, and the sample can be prevented from being damaged. It can be said that this achieves the merits of observation on the process of thin piece formation.

In the embodiment disclosed here, only these process steps are increased: the steps of obtaining the observation image 6 including the overall area and defining the electron beam irradiation permit area 7 and the electron beam irradiation inhibit area 8. Thus, it can be said that influence on the throughput of sample preparation and ease of operation is significantly small. As discussed above, precise machining can be conducted, while changes in the properties of the sample caused by electron beam irradiation are prevented, which achieves the problems.

Embodiment 2

This embodiment is different from embodiment 1 in a method that obtains an observation image 6 to define an electron beam irradiation permit area 7 and an electron beam irradiation inhibit area 8.

In embodiment 1, the electron beam lens barrel 2 scans the area including the thin piece sample 5 with the electron beam for only one time and the observation image 6 is obtained at the point in time at which the remaining thickness of the thin piece sample 5 is a few hundreds nm or above. However, in the embodiment, an observation image is not obtained by scanning the entire area including the thin piece sample 5 for one time. Because the relationship between the thin piece sample and the structure therearound is known in many cases, a portion that is the electron beam irradiation permit area 7 is reliably partially scanned with the electron beam to obtain a part of the observation image 6, and the scan area is extended step by step based on information already known about the structure around the sample, whereby the electron beam irradiation inhibit area 8 can be defined with no irradiation of the electron beam onto the electron beam irradiation inhibit area 8.

Figure 3A:
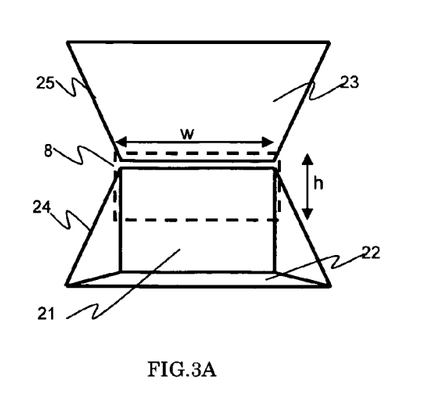
FIGS. 3A and 3B show diagrams illustrative of an observation image sequentially extended in embodiment 2.

A more specific example will be described with reference to FIG. 3. In the example described here, the structure around the thin piece sample is as shown in FIG. 3A. In other words, a hole is formed on both sides of the thin piece portion in a trapezoidal shape that the thin piece portion is the upper base of the trapezoidal shape seen from the top side of the sample in such a way that slopes 22 and 23 are formed as deeper and deeper from outside the hole toward the thin piece. Here, the portion having a height h from the top end of a cross section 21 is the portion desired to be defined as the electron beam irradiation inhibit area 8. In this case, the rectangular electron beam irradiation area is gradually extended from the left end of the screen of the observation image 6 shown in FIG. 1 (from the outside of the portion to form the thin piece portion in the direction in parallel to the thin piece), and beam irradiation is stopped when slope edges 24 and 25 begin to be observed that are the sides connecting to the upper base and the bottom base of the trapezoid.

Figure 3B:
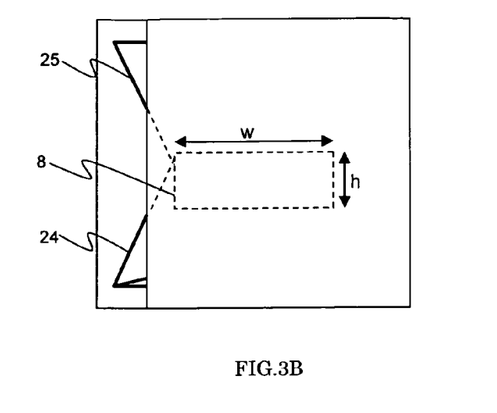

The top end of the cross section 21 can be recognized as the vicinity of the intersection point of the slope edges 24 and 25, and a width w of the cross section 21 is available as information already known. Thus, the electron beam irradiation inhibit area 8 can be determined from the conditions in FIG. 3B, and the area other than the electron beam irradiation inhibit area 8 can be defined as the electron beam irradiation permit area 7.

In machining after this step, the sample is processed while the observation image is observed as only the electron beam irradiation permit area 7 is scanned with the electron beam, whereby precise machining can be conducted, while changes in the properties of the sample caused by electron beam irradiation are prevented, which achieves the problems.

The essence of the invention claimed in the embodiment is as follows. Based on the sample shape clearly known in advance, the area scanned with the electron beam is gradually extended in the electron beam irradiation permit area already known, and the electron beam irradiation inhibit area is estimated from the obtained observation image, whereby the electron beam irradiation permit area 7 and the electron beam irradiation inhibit area 8 are defined in the cross section of the thin piece sample 5 to conduct machining while observation is conducted by electron beam scanning only to the electron beam irradiation permit area 7 with no irradiation of the electron beam onto the area to be the electron beam irradiation inhibit area 8.

Accordingly, it is considered that even a sample in a completely different shape from the shape described in the embodiment can be included in the invention as long as the sample is irradiation permit to this scheme in which the area scanned with the electron beam is gradually extended based on the sample shape clearly known in advance and the electron beam irradiation permit area 7 and the electron beam irradiation inhibit area 8 can be defined with no irradiation of the electron beam onto the area to be the electron beam irradiation inhibit area 8.

Embodiment 3

This embodiment is different from embodiments 1 and 2 in a method that obtains an observation image 6 to define an electron beam irradiation permit area 7 and an electron beam irradiation inhibit area 8. In the embodiment, from the process position determined based on an observation image obtained through the ion beam lens barrel 1, information already known about the depth corresponding to the inhibit area, and the relationship between the beam positions of the ion beam lens barrel 1 and the electron beam lens barrel 2, the electron beam irradiation inhibit area 7 and the electron beam irradiation permit area 8 on the observation image 6 obtained through the electron beam lens barrel 2 are determined by calculation to find a method to define the areas.

Figure 4:
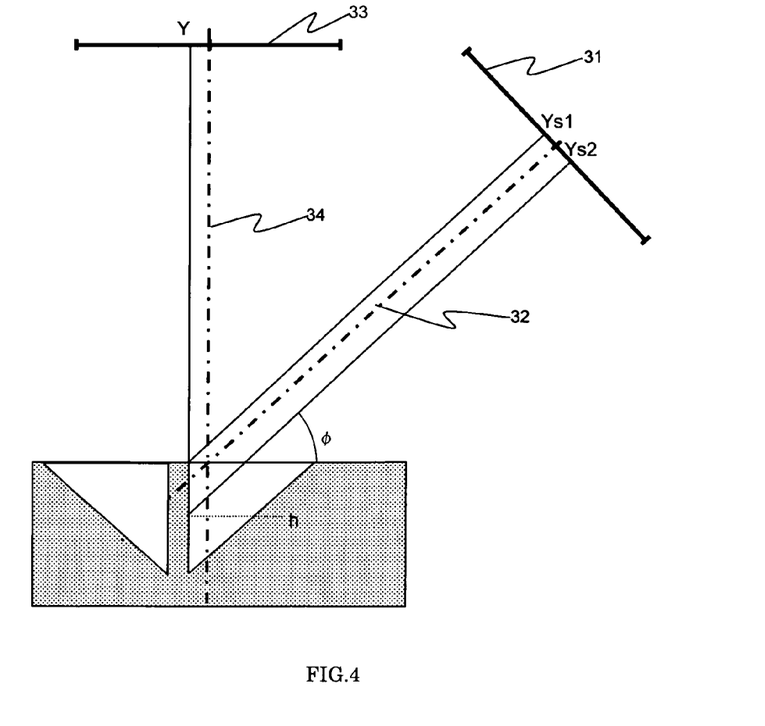
FIG. 4 shows a diagram illustrative of the relationship between positions of an FIB beam and an SEM beam.

As preparation in advance, when the sample surface is at the specified height, adjustment is conducted in such a way that the center of the observation image through the ion beam lens barrel 1 is matched with the center of the observation image through the electron beam lens barrel 2. Moreover, the calibration of the scaling factor and the correction of rotation of field of view are performed. In this state, the sample of the process target is placed at the same specified height as the height when the centers of field of view are matched. In the discussion here, beam axes are defined as follows: the direction orthogonal to both of an ion beam axis 34 of the ion beam lens barrel 1 and an electron beam axis 32 of the electron beam lens barrel 2 is the X-direction, and the direction orthogonal to the X-direction in the screen of the observation image is defined as the Y-direction. On the drawing, the direction penetrating through the paper surface of FIG. 4 is defined as the X-direction. The position in the X-direction on the screen is matched on the observation images through the ion beam lens barrel 1 and the electron beam lens barrel 2 by the adjustment conducted in advance. The Y-direction is influenced by the mounting angle of the electron beam lens barrel 2 and the position in the height direction of the sample. In FIG. 4, a position Ys1 of the cross section at a position Y on an observation image 33 with the ion beam is expressed as follows by a simple geometric calculation from FIG. 4:

$$Ys1 = Y * \sin \phi$$

Although the position in the depth direction is unable to be recognized in the observation image 33 with the ion beam, the position in the depth direction is also able to be recognized in the observation image 31 with the electron beam because the cross section is seen obliquely above. A position Ys2 in the Y-direction that is a location corresponding to a depth h in the cross section is recognized at the position apart from Ys1 by:

$$h * \cos \phi$$

From the discussion above, in the observation image 33 with the ion beam, the range from the top side of the cross section to the depth h existing at the position Y is displayed in the observation image 31 with the electron beam as the following area:

$$\text{the area ranging from } Y * \sin \phi \text{ to } Y * \sin \phi - h * \cos \phi$$

In addition, the width direction of the cross section, that is, the X-direction is matched with that in the observation image 33 with the ion beam because of the adjustment conducted in advance.

According to these relations, information about the process position set based on the observation image through the ion beam lens barrel 1 and information already known about the depth direction are used to determine the electron beam irradiation permit area 7 and the electron beam irradiation inhibit area 8 by calculation. In calculation, changes in the position of the electron beam irradiation inhibit area 8 in the Y-direction are also taken into account, which are caused by changes in the thickness of the sample due to machining. Moreover, because of allowance for error, the electron beam irradiation inhibit area 8 is sometimes properly extended.

In machining after this step, the sample is processed while the observation image is observed as only the electron beam irradiation permit area 7 is scanned with the electron beam, whereby precise machining can be conducted, while changes in the properties of the sample caused by electron beam irradiation are prevented, which achieves the problems.

Embodiment 4

In embodiments 1 to 3 described so far, the electron beam irradiation permit area 7 and the electron beam irradiation inhibit area 8 are fixed. In this embodiment, in each of embodiments 1 to 3, a position recognition target 9 (see FIG. 1) is set in the electron beam irradiation permit area 7. The position recognition target 9 is used to detect a subtle shift in the relationship between the sample and the beam position caused by various unstable factors of the system such as the sample, a stage, and a beam control system, that is, to detect the direction and amount of a so-called drift.

Before the entire electron beam irradiation permit area 7 is scanned with the electron beam, the limited area around the position recognition target 9 is scanned to obtain a position recognition observation image. The coordinates of the position recognition target 9 in the position recognition observation image are checked every time, and the differences from the previous coordinates are considered to be a drift. The electron beam irradiation permit area 7 and the electron beam irradiation inhibit area 8 are moved by this drift, electron beam scanning is then conducted, and an observation image is obtained. For the position recognition target 9, for example, a portion of the characteristic shape on the sample is used for pattern recognition, or such a shape is used for pattern recognition that the shape is formed on the sample with the ion beam lens barrel 1 and easily seen. In addition, the area of obtaining the position recognition observation image is determined in consideration of the size of the position recognition target 9 and an amount of a drift usually thought.

With this method, even though a drift occurs, the sample is machined while the observation image is observed as only the electron beam irradiation permit area 7 is scanned with the electron beam, whereby precise machining can be conducted, while changes in the properties of the sample caused by electron beam irradiation are prevented, which achieves the problems.

Embodiment 5

Figure 5:
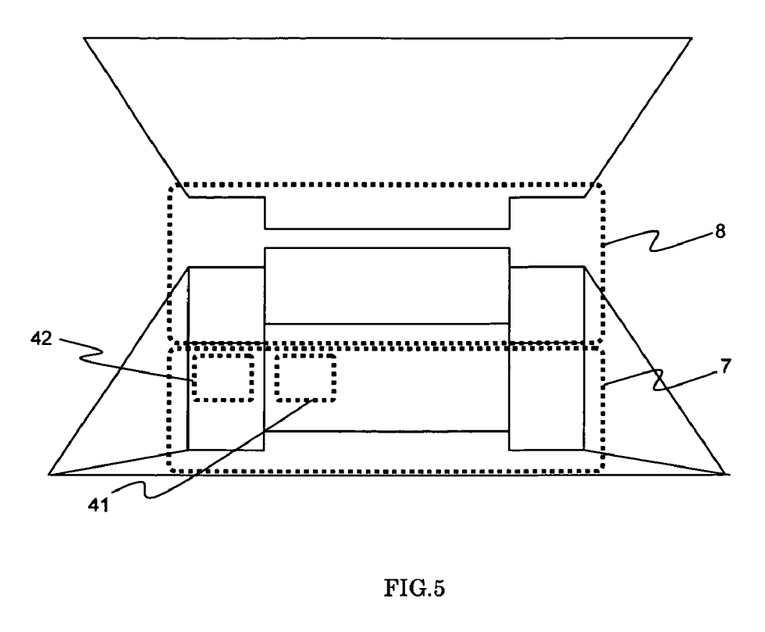
FIG. 5 shows a schematic perspective view depicting a portion including a thin piece sample in embodiment 5.

FIG. 5 shows a schematic perspective view depicting a portion including a thin piece sample 5 for a fifth embodiment according to the invention.

In embodiments 1 to 4, the defined electron beam irradiation permit area 7 is scanned with the electron beam to obtain the observation image, and precise machining is implemented based on information acquired from the observation image. In this embodiment, such a method is disclosed that the thickness of the thin piece sample 5 is estimated from an amount of secondary signals emitted from the thin piece sample 5 caused by electron beam irradiation and machining is terminated in a predetermined thickness. In each of embodiments 1 to 4, when the electron beam irradiation permit area 7 exists at least in a part of the thin piece sample 5, a thickness monitoring area 41 is defined inside the electron beam irradiation permit area 7 on the thin piece sample 5. In addition, a sufficiently thick area is defined inside the electron beam irradiation permit area 7 as a reference area 42.

Generally, when the electron beam is applied onto the thin piece sample, in the area that is thinner than the penetration length of the electron beam determined depending on the energy of the electron beam and the material of the sample, the amount of secondary signals changes according to the thickness of the thin piece sample. The energy of the electron beam is suitably selected to keep track of changes in secondary signals, whereby the thickness of the sample can be estimated. For the secondary signal, secondary electrons, reflection electrons, absorption current, X-rays, and transmission electrons can be used. However, in the discussion below, an example using reflection electrons will be described.

In embodiments 1 to 4, a secondary electron detector is used for the secondary signal detector 3. However, in the embodiment, a reflection electron detector is used. In the area in which the thickness of the thin film is thinner than the penetration length of the incident electron beam, the intensity of reflection electrons from a thin film sample includes information about the thickness of the sample. More specifically, the signal amount is decreased as the thickness of the sample becomes thinner and thinner. Thus, at the point in time at which the intensity of reflection electrons is decreased to a certain value, it is determined that the thickness reaches the target thickness, and then machining is terminated. In other words, in order to cancel variations in the system, as shown in FIG. 5, such a value is used as the index of the thickness that the intensity of reflection electrons from the thickness monitoring area 41 is normalized by the intensity of reflection electrons from the reference area 42.

According to this method, machining is conducted while the thickness of the sample is monitored as the electron beam is applied only onto the electron beam irradiation permit area 7, whereby precise machining can be conducted, while changes in the properties of the sample caused by electron beam irradiation are prevented, which achieves the problems.

Embodiment 6

In this embodiment, a method of observing cross section processing as an example is shown that a cross section image of a desired part (defect portion) in a sample is obtained.

Figure 6:
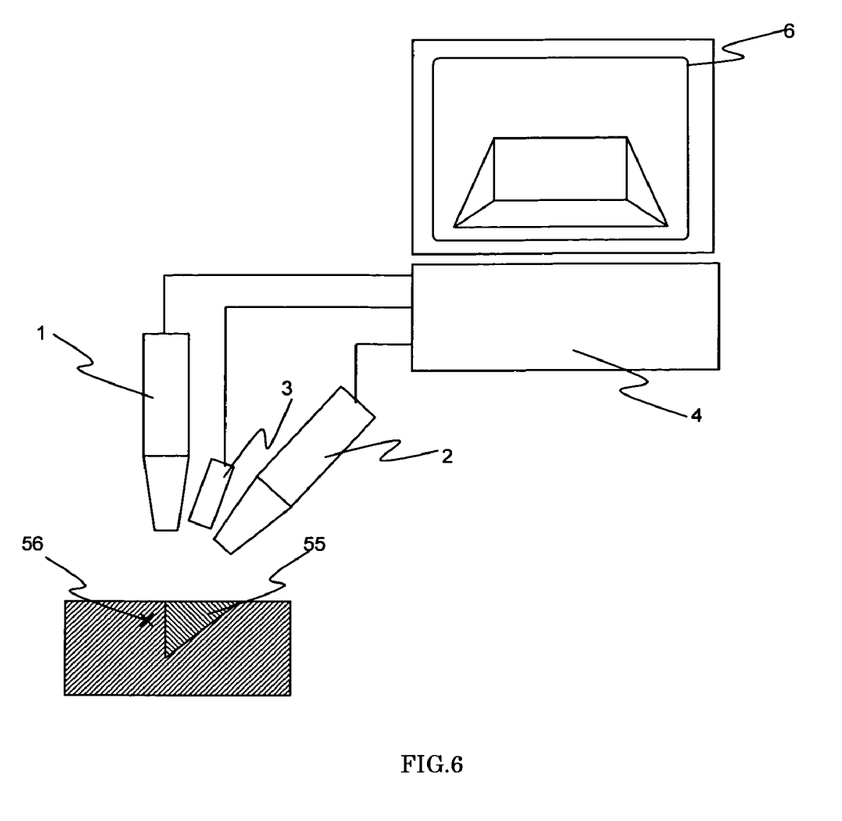
FIG. 6 shows a diagram illustrative of the configuration of embodiment 6.
Figures 7A, 7B:
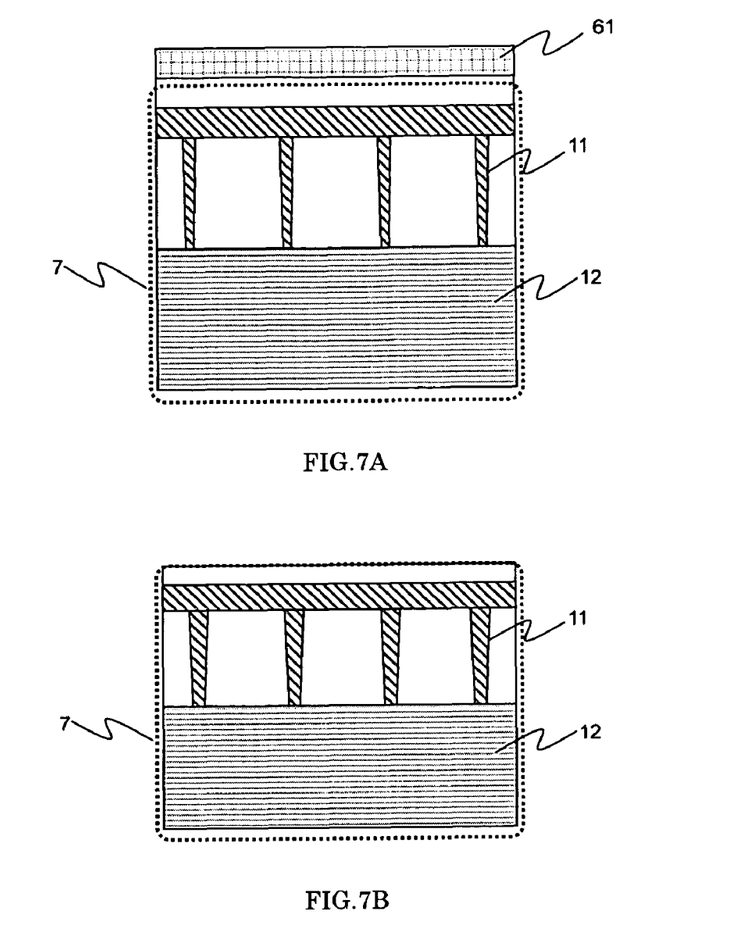
FIGS. 7A to 7C show structural diagrams depicting the section of a sample obtained in embodiment 6.

As shown in FIG. 6, a sample is etched by the ion beam lens barrel 1 to form a process groove 55 near a defect portion 56 that is a desired part, and the cross section image of the sample is obtained with an ion beam or with an electron beam having a small amount of current. FIG. 7A shows a cross section image of a sample of a semiconductor device obtained according to the method above, which is different from one shown in FIG. 2 in that the sample does not include an interlayer insulating film of a material that is changed in the properties by electron beam irradiation but the sample includes a passivation layer 61 on the sample surface. The electron beam is applied onto the passivation layer 61 to cause charge-up, which affects the electron beam to be applied and the observation image. Thus, it is desired that the electron beam irradiation to this layer is avoided as much as possible. Then, control is conducted in such a way that the electron beam irradiation permit area 7 is defined so as to avoid the passivation layer 61 and the electron beam is applied only onto the electron beam irradiation permit area 7 until cross section processing reaches a desired part, and then a cross section image is obtained.

Figure 7C:
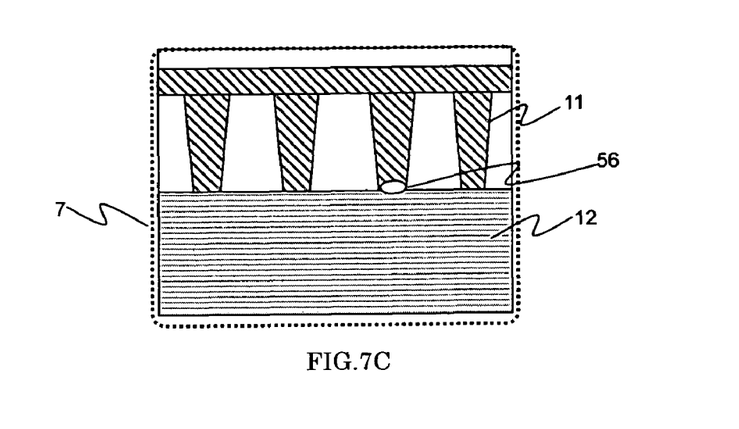

The cross section of the sample in the process groove 55 is etched by ion beam processing to expose a new cross section. FIG. 7B shows a cross section newly shown, which is a new cross section image obtained by irradiating the electron beam onto the electron beam irradiation area 7. The processing of the cross section by ion beam irradiation and the observation of a new cross section are repeatedly conducted until the cross section of a desired part of the defect portion 56 is exposed. A new cross section exposed by ion beam processing is checked in the observation image, whereby such an event can be prevented that a desired part is missed and the sample is excessively processed, and ion beam processing can be terminated at the time when the cross section of a desired part is exposed. FIG. 7C shows a cross section observation image including the defect portion 56 obtained by repeating ion beam processing and cross section observation. As described above, cross section processing and cross section observation are repeated, in which electron beam irradiation is avoided to the portion that is desired to avoid electron beam irradiation as much as possible, whereby the cross section image of a desired part can be obtained, which achieves the problems.

Other Embodiments

In the embodiments described above, for the ion beam lens barrel 1, a focused ion beam apparatus is considered which uses liquid metal gallium as an ion source. However, precise machining can be also conducted by using focused ion beam apparatuses using the other ion sources, or ion beam apparatuses with a gas ion source using a noble gas or an inert gas with a larger beam diameter, while changes in the properties of the sample caused by electron beam irradiation are prevented, which can achieve the problem.

What is claimed is:

1. A composite charged particle beam apparatus comprising:
   an ion beam lens barrel configured to etch a sample with an ion beam;
   an electron beam lens barrel configured to irradiate an electron beam onto a given area on the sample;
   a secondary signal detector configured to detect a secondary signal generated by electron beam irradiation;
   a data processing unit configured to associate a position to irradiate an electron beam with an amount of secondary signals for imaging;
   an image display unit configured to display thereon an image of a given area on the sample based on an image signal from the data processing unit;
   an irradiation position setting means for defining an irradiation permit area or an irradiation inhibit area specified by an input device as electron beam irradiation position data; and
   an irradiation position control unit configured to control a position to irradiate an electron beam based on electron beam irradiation position data from the irradiation position setting means,
   wherein the irradiation position setting means updates electron beam irradiation position data depending on whether the specified area is an irradiation permit area or an irradiation inhibit area, whereby the irradiation position control unit restricts electron beam irradiation only to the irradiation permit area.

2. The composite charged particle beam apparatus according to claim 1,
   wherein the irradiation position setting means updates electron beam irradiation position data from the irradiation permit area and the irradiation inhibit area, both areas specified by the input device, in an image including an entire etching process area obtained by ion beam scanning in advance.

3. The composite charged particle beam apparatus according to claim 1,
   wherein during processing with an ion beam, the irradiation position setting means estimates an electron beam irradiation permit area from an image at a position apart from a process target area and information already known about a sample process target portion.

4. The composite charged particle beam apparatus according to claim 1,
   wherein the secondary signal detector is capable of detecting a secondary signal generated by ion beam irradiation,
   the data processing unit associates an ion beam irradiation position with an amount of secondary signals for imaging, and
   the irradiation position setting means defines an electron beam irradiation permit area and an electron beam irradiation inhibit area based on a relationship between relative positions of an ion beam and an electron beam from an observation image with an ion beam.

5. A method of processing a sample using the composite charged particle beam apparatus according to claim 1, the method comprising the steps of:
   setting a position recognition target in an observation image of an irradiation permit area;
   detecting a relative position shift between a position of a sample and a position to irradiate an electron beam based on a movement of the target; and
   correcting a position of the irradiation permit area.

6. A method of processing a sample using the composite charged particle beam apparatus according to claim 1, the method comprising the steps of:
   detecting an amount of secondary signals from an irradiation permit area; and
   terminating ion beam etching when an amount of secondary signals reaches a predetermined amount.

7. The method of processing a sample using the composite charged particle beam apparatus according to claim 6, the method comprising the steps of:
   obtaining an observation image formed by secondary signals generated by an electron beam, the image including an entire process area;
   defining a thickness monitoring area and a reference area as an irradiation permit area in the observation image;
   irradiating an electron beam only onto the irradiation permit area; and
   detecting a secondary charged particle generated in the thickness monitoring area and the reference area, calculating thickness information about the thickness monitoring area from amounts of the detected secondary charged particles, and terminating ion beam etching when the calculated thickness reaches a consumed thickness.

8. A method of preparing a sample for a transmission electron microscope using a composite charged particle beam apparatus, the apparatus including: an ion beam lens barrel configured to etch a sample with an ion beam; an electron beam lens barrel configured to irradiate an electron beam onto a given area on the sample; a secondary signal detector configured to detect a secondary signal generated by electron beam irradiation; a data processing unit configured to associate a position to irradiate an electron beam with an amount of secondary signals for imaging; and an image display unit configured to display thereon an image of a given area on the sample based on an image signal from the data processing unit, wherein a condition of a sample in the process of etching with an ion beam is observed, the method comprising:
   after conducting etching with an ion beam to prepare a sample with a thin piece portion having a predetermined thickness thicker than a finishing thickness;
   a first step of obtaining an electron beam observation image of an entire cross section of the thin piece portion;
   a second step of defining an irradiation area and an irradiation inhibit area in the observation image; and
   a third step of cutting a thin piece in the finishing thickness while the thickness is monitored as irradiation of the electron beam is restricted only to the irradiation permit area.

9. A method of preparing a sample for a transmission electron microscope using a composite charged particle beam apparatus, the apparatus including: an ion beam lens barrel configured to etch a sample with an ion beam; an electron beam lens barrel configured to irradiate an electron beam onto a given area on a sample; a secondary signal detector configured to detect a secondary signal generated by electron beam irradiation; a data processing unit configured to associate a position to irradiate an electron beam with an amount of secondary signals for imaging; and an image display unit configured to display thereon an image of a given area on the sample based on an image signal from the data processing unit, wherein a condition of a sample in the process of etching with an ion beam is observed, the method comprising the steps of:
    forming a hole on both sides of a thin piece portion in a trapezoidal shape in which the thin piece portion is an upper base of the trapezoidal shape of the hole seen from the top side of a sample when the thin piece portion is prepared with an ion beam in a predetermined thickness thicker than a finishing thickness;
    obtaining an observation image that is a part of a shape having a side connecting to a bottom base of the trapezoidal shape with respect to the hole on both sides while a rectangular electron beam scan area is brought close to a hole process portion on both sides from outside the hole process portion on both sides in parallel to the thin piece portion;
    determining an electron beam irradiation inhibit area and an electron beam irradiation permit area in a thin piece portion cross section from the observation image and a length of the thin piece portion; and
    irradiating an electron beam onto the electron beam irradiation permit area to cut the thin piece portion in a finishing thickness with an ion beam while the thickness is monitored.

\* \* \* \* \*

UNITED STATES PATENT AND TRADEMARK OFFICE
CERTIFICATE OF CORRECTION

PATENT NO.       : 7,973,280 B2
APPLICATION NO.  : 12/378138
DATED            : July 5, 2011
INVENTOR(S)      : Haruo Takahashi et al.

It is certified that error appears in the above-identified patent and that said Letters Patent is hereby corrected as shown below:

Title Page,
IN THE HEADING, ITEM (73)
    "SII Nanotechnology Inc." should read --SII NanoTechnology Inc.--.

Signed and Sealed this
Thirteenth Day of September, 2011

David J. Kappos
*Director of the United States Patent and Trademark Office*